(12) United States Patent
Guelat et al.

(10) Patent No.: US 7,918,856 B2
(45) Date of Patent: Apr. 5, 2011

(54) GUIDED REAMER SYSTEM FOR RESHAPING BONE

(75) Inventors: Didier Guelat, Bure (CH); Andre Lechot, Orvin (CH)

(73) Assignee: Greatbatch Medical S.A., Orvin (CH)

( * ) Notice: Subject to any disclaimer, the term of this patent is extended or adjusted under 35 U.S.C. 154(b) by 1131 days.

(21) Appl. No.: 11/617,743

(22) Filed: Dec. 29, 2006

(65) Prior Publication Data
US 2007/0173847 A1 Jul. 26, 2007

Related U.S. Application Data

(63) Continuation-in-part of application No. 10/266,442, filed on Oct. 8, 2002, and a continuation-in-part of application No. 11/117,740, filed on Apr. 29, 2005.

(60) Provisional application No. 60/783,788, filed on Mar. 17, 2006, provisional application No. 60/783,921, filed on Mar. 20, 2006.

(51) Int. Cl.
*A61B 17/00* (2006.01)

(52) U.S. Cl. .............................. 606/80; 606/81; 606/89

(58) Field of Classification Search .................... 606/80, 606/89
See application file for complete search history.

(56) References Cited

U.S. PATENT DOCUMENTS

| | | | |
|---|---|---|---|
| 3,633,583 A | 1/1972 | Fishbein | |
| 4,116,200 A | 9/1978 | Braun et al. | |
| 4,284,080 A * | 8/1981 | Rehder | ............................ 606/80 |
| 5,376,092 A | 12/1994 | Hein et al. | |
| 5,658,290 A | 8/1997 | Lechot | |
| 5,968,049 A | 10/1999 | Da Rold | |
| 5,976,144 A | 11/1999 | Fishbein et al. | |
| 6,106,536 A * | 8/2000 | Lechot | ........................... 606/180 |
| 6,129,732 A | 10/2000 | Lechot | |
| 6,162,227 A | 12/2000 | Eckhardt et al. | |
| 6,475,221 B1 | 11/2002 | White et al. | |

(Continued)

FOREIGN PATENT DOCUMENTS
EP 0 782 840 7/1997
(Continued)

*Primary Examiner* — Eduardo C Robert
*Assistant Examiner* — Andrew Yang
(74) *Attorney, Agent, or Firm* — Michael F. Scalise

(57) ABSTRACT

A guided reamer (10) has a central cannulation (12, 12a) adapted to receive a drill pin (14) secured in a manner which is axially aligned with the stem (22) of the bulbus bone joint (20). The reamer (10) has a profile cutting form (24) with cutting teeth (40) formed therein for cutting a form of a defined profile. The reamer (10) has a circumferential rim (34) having rim cutting teeth (36) disposed to cut to an outside of the rim and an inside of the rim, having face cutting teeth (37) adapted to cut an annular channel into bone and a plurality of planing teeth (52) radially disposed on an internal surface adjacent an axial end boss (44). The cannulation (12, 12a) is supported at the apex of the cutting form (24) and is formed in a guide assembly (70, 70') affixed to the apex. The guide assembly (70, 70') is adapted for imparting rotation to the reamer (12). The reamer (10) is adapted to be supported by a cannulated reamer handle (74) having a bayonet locking device (76) capable of locking the handle (74) to the guide assembly (70, 70') of the cannulated reamer (10) and a corresponding central cannulation (86), permitting the drill pin (14) to pass at least part way therethrough.

28 Claims, 6 Drawing Sheets

| U.S. PATENT DOCUMENTS | | | | FOREIGN PATENT DOCUMENTS | | |
|---|---|---|---|---|---|---|
| 2004/0193168 A1* | 9/2004 | Long et al. ............ 606/80 | | FR | 2554709 | 5/1985 |
| 2005/0075639 A1 | 4/2005 | Lechot | | WO | WO 99/47051 | 9/1999 |
| 2005/0251145 A1 | 11/2005 | Desarzens et al. | | WO | WO00/62718 | 10/2000 |
| 2006/0095041 A1 | 5/2006 | Fehlbaum et al. | | * cited by examiner | | |

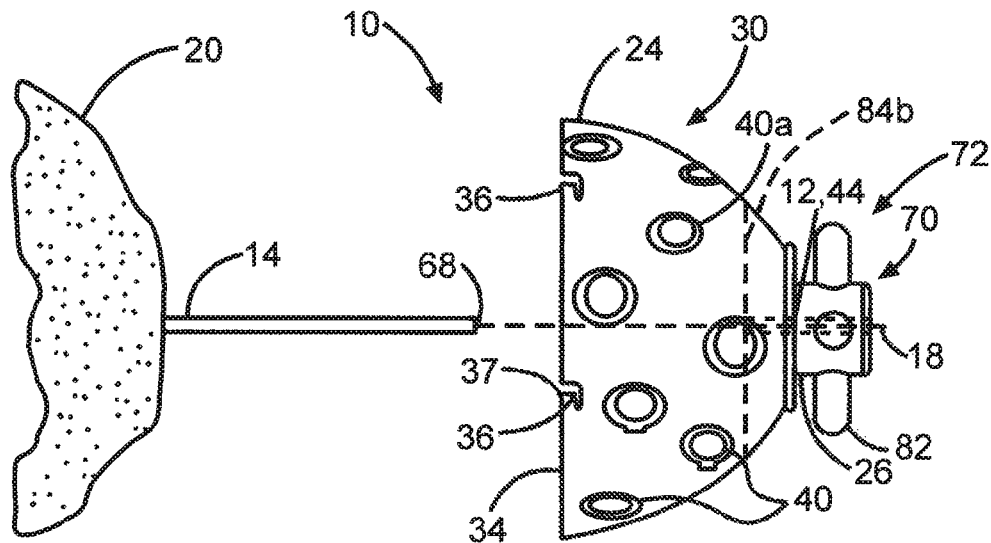
FIG. 1A
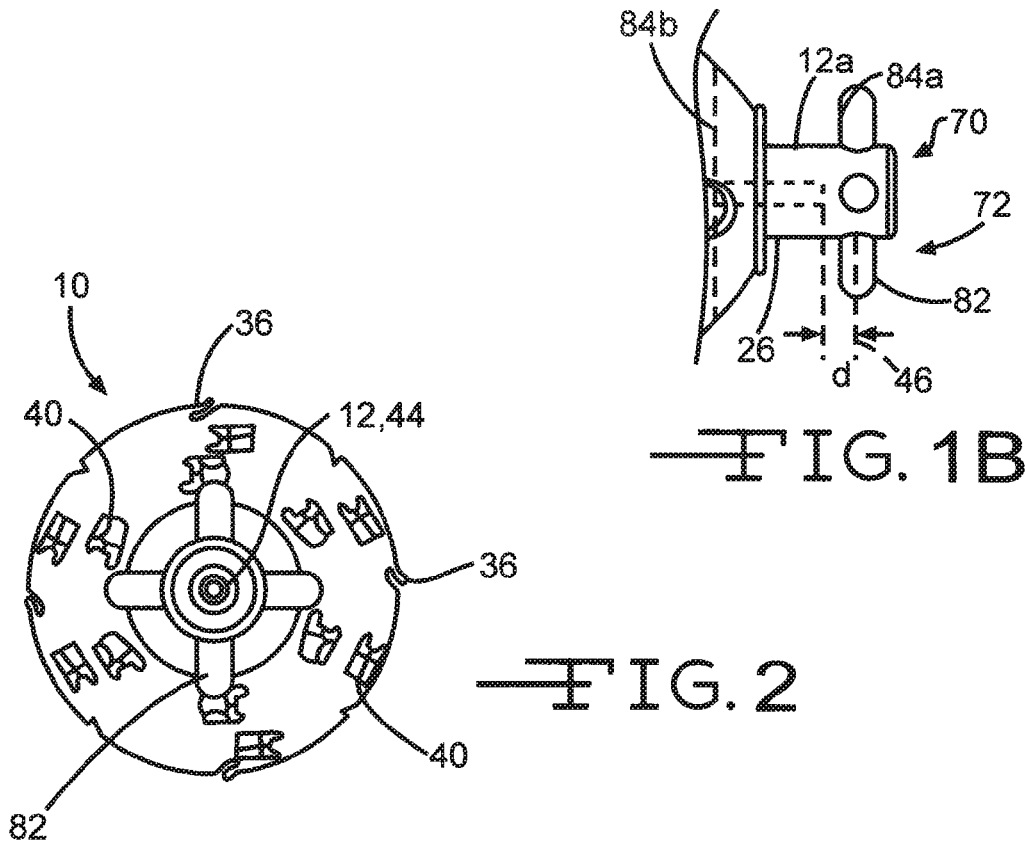
FIG. 1B
FIG. 2

US 7,918,856 B2

GUIDED REAMER SYSTEM FOR RESHAPING BONE

CROSS REFERENCE TO RELATED APPLICATIONS

This application is a continuation-in-part application of U.S. application of the same name, Ser. No. 11/117,740, filed 29 Apr. 2005 and U.S. application Ser. No. 10/266,442, entitled ACETABULAR REAMER, filed Oct. 8, 2002, and claims priority under the Paris Convention to U.S. provisional applications entitled Inverted Reamer with Rim Cutting Teeth, Ser. Nos. 60/783,788 and 60/783,921, filed on Mar. 17, 2006 and Mar. 20, 2006, respectively, the contents of all of which are incorporated herein by reference and relied upon.

BACKGROUND OF THE INVENTION

The present invention is in the field of surgical devices for use in preparing a bone site for receiving a prosthesis. More specifically, the present invention relates to surgical tool head attachable to a surgical instrument holder.

The invention relates to a bone shaping system made up of an instrument holder and a surgical instrument, i.e., a surgical tool head, for attachment to the holder. The holder includes a shank equipped with a head designed to receive an instrument, and an annular locking component mounted so as to slide about the shank, under the head, equipped with locking means which cooperate with the head so as to lock the instrument on the head, and pushed against the head by a helical spring. The present surgical tool head is disposed to mate with an attach to the head of the tool holder. An example of a tool holder suitable for practice with the present invention is disclosed in US Patent Application Publication No. 2005/0251145, the content of which is incorporated herein by reference.

One such system is described in European Patent 0782840, the content of which is incorporated herein by reference thereto, and includes a shaft (10), equipped at one end with a cutting head holder (12) which has a bayonet joint and lock. A hemispherical or conical rotary cutting head (1) has inner radial rods (4) to engage with the bayonet joint. The cutting head contains an axial guide tube (5) between the inner ends of the radial rods and a central aperture (3) to receive a twist drill (9) which makes a hole in the middle of the recess formed by the cutting head. The lower end of the guide tube has one or more notches to receive corresponding studs on the twist drill so they rotate together.

Other systems provide for reshaping of the bone, but the tool itself generally obstructs the view of the bone lobe during cutting.

A total hip replacement procedure removes the organic stem of a bulbus bone joint replacing it with an artificial one. This is a relatively radical surgical procedure, and alternative processes exist that attempt to preserve the natural joint. One such procedure places a hard, external prosthetic cap over a resurfaced bulbus bone joint. The cap has an external spherical surface which mates with a hip socket. The cap is often made of metal and has precise interface dimensions which must be matched to the bone of the joint in order for the cap to properly fit over the joint, and to properly function in its corresponding prosthetic hip socket.

Therefore, there is a need for cutters capable of cutting and shaping the bulbus bone joint in preparation for the reception of a prosthetic cap. Such an application presents other challenges in guidance and control, particularly that of ensuring that the stem of the bulbus bone joint is not damaged in the process. Still further, what is needed therefore is a system which enables controlled cutting and reshaping of the bulbus bone joint in preparation for the reception of a bone cap prosthesis. In particular, what is needed is a reamer capable of cutting the bulbus bone joint to closely receive a bulbus bone joint prosthetic cap.

SUMMARY OF THE INVENTION

A reamer system is provided which includes a cannulated reamer handle, and a corresponding cannulated reamer, which, when assembled and operated over a drill pin secured in a manner axially aligned with the stem of the bulbus bone joint, enables the accurate and controlled reshaping of the bulbus bone joint. The reamer is made up of a cutting form and a central guide, in which the guide supports a bar structure. The bar structure includes portions which connect to and extend radially from a central guide. Optionally, the central guide includes a surface offset from a plane of the bar structure to a degree which enables that surface to contact an associated surface referenced to the bone, in order to prevent the cutting form from plunging so far over the bone as to potentially damage the bulbus bone stem. This offset surface is preferably polished to reduce friction during relative rotational movement between this surface and the surface referenced to the bone. The offset surface is an axially perpendicular surface of a boss through which the drill pin is guided.

In an advantage, the invention is a combination inverted reamer having the advantage of being a single part with fewer operative steps, thereby reducing surgical time and increasing accuracy. The combination is enabled because of a superior design of cutting teeth that has a lower cutting torque and thus allows a cut on multiple simultaneous surfaces.

An object of the invention is to provide a device for concurrently cutting and shaping the bulbus bone joint in preparation for the reception of a prosthetic cap.

Another object of the invention is to provide a guided means of cutting and shaping the bulbus bone joint while not damaging it in the process.

Another object of the invention is to provide a system which enables controlled cutting and reshaping of the bulbus bone joint in preparation for the reception of a bulbus bone cap prosthesis.

Another object of the invention is to provide a device capable of cutting the bulbus bone joint to closely receive a bulbus bone joint prosthetic cap.

BRIEF DESCRIPTION OF THE DRAWINGS

FIG. 1A is a side plan view of a guided reamer with rim cutting teeth of the present invention, with the reamer disposed to be engaged with a guide pin set in a femur joint.

FIG. 1B is a partial side plan view of a guided reamer surgical tool head wherein the guide assembly is adapted to have a blind-ended guide bore to provide a depth of cut stop.

FIG. 2 is a top plan view of an alternative embodiment of the present guided reamer surgical tool head with rim cutting teeth, showing alternate inside and outside cutting teeth.

DETAILED DESCRIPTION OF THE PREFERRED EMBODIMENT(S)

Figure 3:
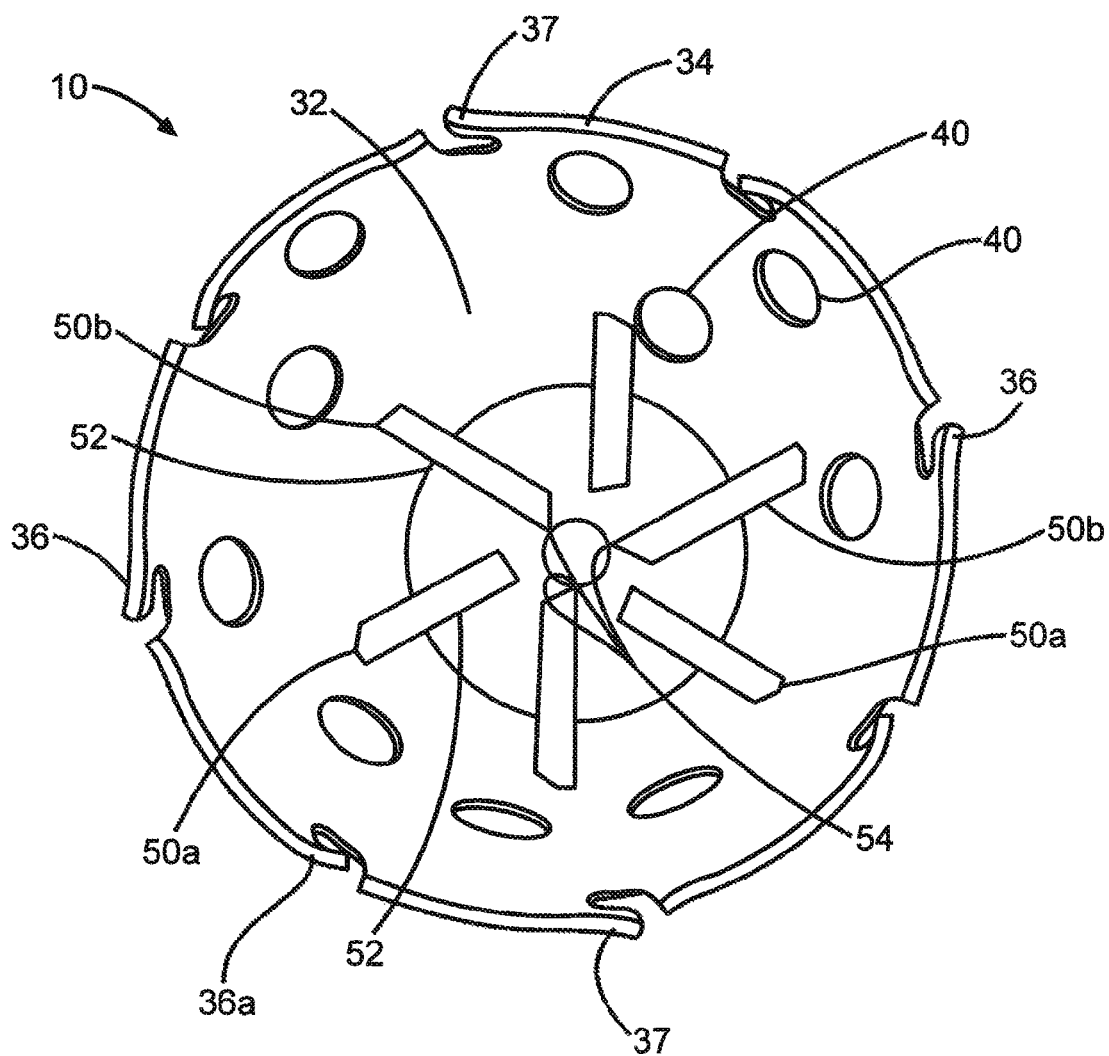
FIG. 3 is a perspective view of the present inverted reamer surgical tool head with rim cutting teeth, showing the inside of the reamer of FIG. 1.

Referring now to the drawings, the details of preferred embodiments of the present invention are graphically and schematically shown. Like elements in the drawings are represented by like numbers, and any similar elements are represented by like numbers with a different lower case letter suffix.

Figure 4A:
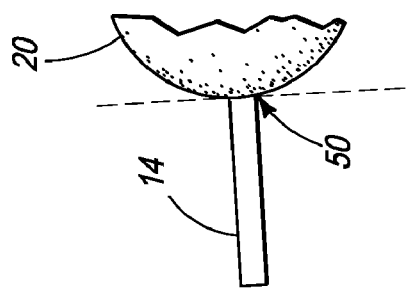
FIG. 4A is a partially expanded side view of the reamer and holder assembly of the invention, ready to be received at the operation site.
Figure 4A:
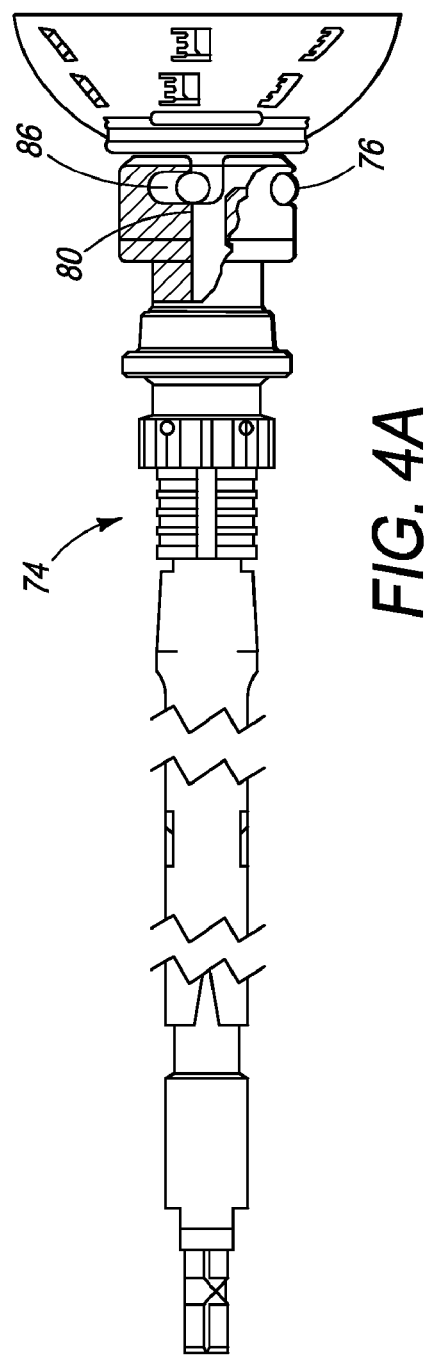
Figure 4B:
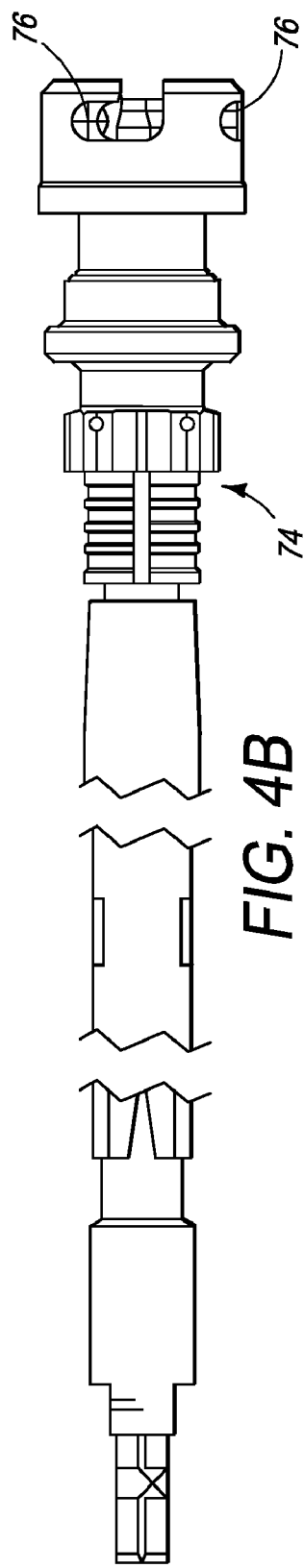
FIG. 4B is a side view of the reamer holder of the system of the invention.
Figure 4C:
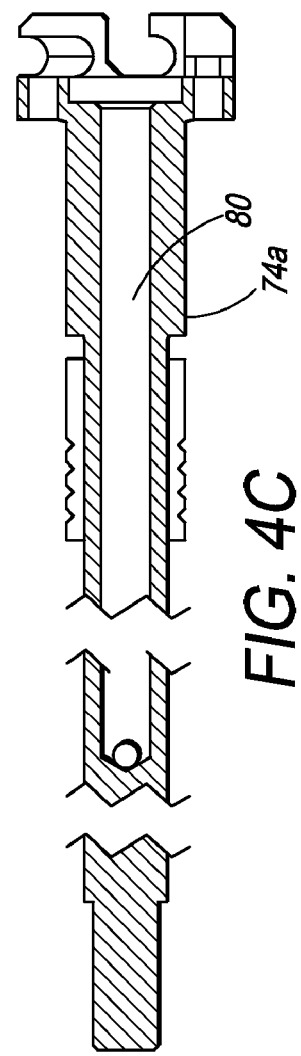
FIG. 4C is a side view of the shaft of the holder of the system of the invention.
Figure 5A:
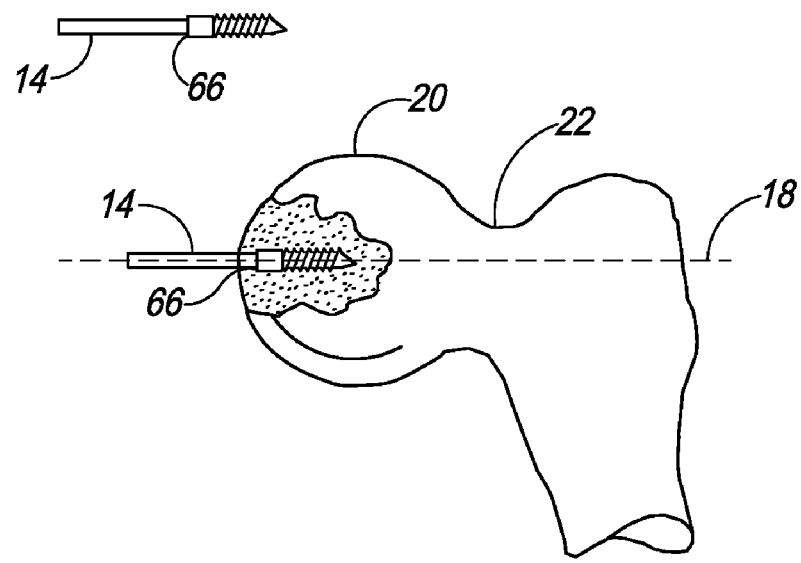
FIGS. 5A and 5B are side views of the stem of bulbus bone joint with a guide pin in place before and after use of the present tool head to shape the stem.

As shown in FIGS. 1A and 1B and FIGS. 2 to 3, the cannulated reamer 10 has a central guide bore (cannula) 12, 12a adapted to receive a guide or drill pin 14 secured in an appropriate manner in the femur or humerus bone joint 20 (preferably in a manner axially aligned with the stem 22 shown in FIG. 5A). In a preferred embodiment, the present reamer 10 is assembled in combination with a reamer handle (see FIGS. 4A-4C). The combination reamer handle and reamer head 10 is operable over a guide pin 14 affixed securely to the joint 20 usually by torquing into a pre-drilled hole. The guide pin 14 is axially aligned with reamer head 10 in an appropriate orientation with the joint 20. The present reamer 10 with rim cutting teeth 36, 37, and form cutting teeth 40, formed for example as described in US patent publication no. 20050075639, entitled "Contour Reamer Teeth" and US Patent publication no. 20060095041, entitled "Contour Reamer Teeth and Method of Manufacture" (the contents of which are incorporated herein by reference) enables the accurate and controlled shaping of the bulbus bone joint 20 to receive the prosthetic cap 90 of a prosthetic hip joint. In the preferred embodiment, the central guide bore 12 was sized and surface treated to be a precise, sliding fit with the drill guide pin 14, in order to provide the necessary axial guidance to the reamer 10 when cutting bone joint 20. The reamer 10 has a profile cutting form 24 (for cutting a spherical, conical, or other form) defined by its having an inside surface 32 (shown in FIG. 3) that provides a specific cutting profile configured to enable the bulbus bone joint 20 after reaming to closely mate with a prosthetic cap 90 (shown in FIG. 5B). The present reamer 10 differs from a traditional acetabular reamer (not shown) which typically cuts a concave form in a bone socket. In contrast, the present reamer 10, for example, cuts a form onto the external surfaces of bulbus bone joint 20. In other words, the profile cutting reamer shown cuts the joint 20 so as to maintain a convex cross-section, characterized by having a second derivative which is a positive number, as opposed to a traditional acetabular reamer which cuts a concave form, characterized as having a negative second derivative. Consequently, as mentioned above, the system, designed to cut bulbus bone surfaces, is quite different from prior art systems which cut convex surfaces.

The cannulation 12, 12a is supported by an axial end boss 44, such as about an apex of the cutting form 24 and formed in an axial guide assembly 70 affixed to an axial end. An axial drive interface 72 is affixed to the reamer 10 adjacent the axial end boss 44, this interface adapted for imparting rotation to the reamer. The cannulation 12 in the reamer 10 is a clearance hole 12 but may also be a blind hole 12a. The cannulation 12, 12a is sized and surface treated to be a precise, sliding fit with the drill pin 14, in order to provide substantially all the axial guidance to the reamer when cutting bone 20.

Additionally, the present reamer has cutting teeth 36, set into the rim 34 of the concave cutting head 30, as well as cutting teeth 40 formed in the wall of the inside surface 32 of the form-cutting cutting head 30. FIGS. 1A to 3 illustrate three different types of cutting teeth 36, beyond the more conventional cutting teeth 40 located on the form cutting body of the reamer 10. In the preferred embodiment, the rim cutting teeth 36 are disposed with a pitch to cut either to the outside of the rim 34 and or to the inside of the rim (see FIG. 3). Also, the rim cutting teeth 36 had a downward cutting face 37 as well (see FIGS. 1A to 3). The inside-to-outside pitch of the cutting teeth 36 is important, and is set to permit the rim 34 to cut a leading-edge trough 60 (see FIG. 5B) as the reamer 10 cuts away the surface of the joint 20. The capability to cut a leading edge trough 60 may not be needed in every application, but in those where it is useful, the pitch width of the cutting teeth 36 is set to provide a trough 60 disposed to closely receive the rim of the prosthetic cap 90 to be fitted to the joint 20. Also note, as shown in FIG. 3, the inside rim cutting teeth 36a are disposed in relation to the nearest circle of surface teeth 40a to provide an overlapping cutting action.

The cannulation 12, 12a in the guide assembly 70 is sized and surface treated to be a precise, sliding fit with the drill pin 14, in order to provide substantially all axial guidance to the reamer 10 when cutting bone 20.

The guide assembly 70 includes a surface 84a and/or 84b in a plane parallel to a plane 46 of the at least one bar 82, optionally offset at a distance d which enables that surface 84b to contact an associated surface 68 referenced to the bone 20, in order to prevent the cutting form 24 from plunging so far over the bone as to potentially damage the bulbus bone stem 22 or to cut more bone away than required to fit the prostheses 90. The offset surface 84 is preferably polished to reduce friction during relative rotational movement between this surface 84 and the surface 68 referenced to the bone 20.

In addition to the rim teeth 36, face cutting teeth 37, and the surface teeth 40, the present reamer 10 had a third set of cutting teeth. As shown in FIG. 3, the third set of cutting teeth are planing teeth set adjacent the axial end boss 44 of the cutting head's interior surface 32. The planing teeth were of type types: the shorted type 50a had a side cutter 52, and the longer type 50b had both a side cutter 52 and an end cutter 54. The end cutter 54 of the long planing teeth 50b provided for trimming away material adjacent the guide pin 14 as the reamer 10 was advanced down the pin 14. The side cutter 52 of both types of planing teeth 50a and 50b provided for flattening the joint 20 adjacent the guide pin 14. The combination of the different cutting features of the reamer 10 provide a formed bulbus bone joint 20 having, for example, characteristics shown in FIG. 5B.

Referring now to FIGS. 4A to 4C, the reamer 10 is adapted to be supported by a cannulated reamer handle 74 including a bayonet locking device 76 capable of locking the handle 74 to the drive interface 72 of the reamer. The handle 74 has a corresponding central cannulation 80, permitting the drill pin 14 to pass at least part way therethrough. The bayonet locking mechanism 76 includes recesses 86 which catch portions of the bar structure 03. The drive interface 72 is comprised of at least one bar 82, traversing a center of the boss 26, 26'. However, four or more bars 82, preferably, evenly spaced about the boss 26, 26', may also be used. The bar structure 30 is made up of a hollow post 26' attached to an axial end boss 44 of the cutting form 24, with bars 32 attached thereto which are axially spaced apart and which extend radially out from the post.

The cannulated reamer handle 34 has a bayonet locking device 36 capable of locking the handle 34 to the cannulated reamer 12 and a corresponding central cannulation 40, permitting the drill pin 16 to pass therethrough. The bayonet locking mechanism 36 includes recesses 56 which catch portions of the bar structure 30.

The guide assembly 70 has bars 30', such as those disclosed in US Patent publication 2005/0251145, the content of which is incorporated herein by reference, which enable the attachment of the reamer tool 10 to a tool handle (not shown) and for properly aligning the cutting features of the tool head 30 with the bulbus bone joint 20. However, other attachment features 74 are known to and are adaptable by one of ordinary skill in the art for practice in the present invention. Alignment is accomplished by the guide assembly having an axial guide bore 12 sharing a common axis 18 with the domed cutting head 30. The axial guide bore 12 passes through the cutting head 30 as well as the guide assembly 70. In an alternative embodiment shown in FIG. 1B, the guide bore 12a is blind-ended. There is a further means of preventing the reamer 10 from cutting too deeply into the joint 20. This is accomplished in this embodiment by the proximal end 68 of the guide pin 14 coming against the blind-end of the guide bore 12a and stopping the guide assembly 70 from sliding further down the guide pin 14.

Figure 5B:
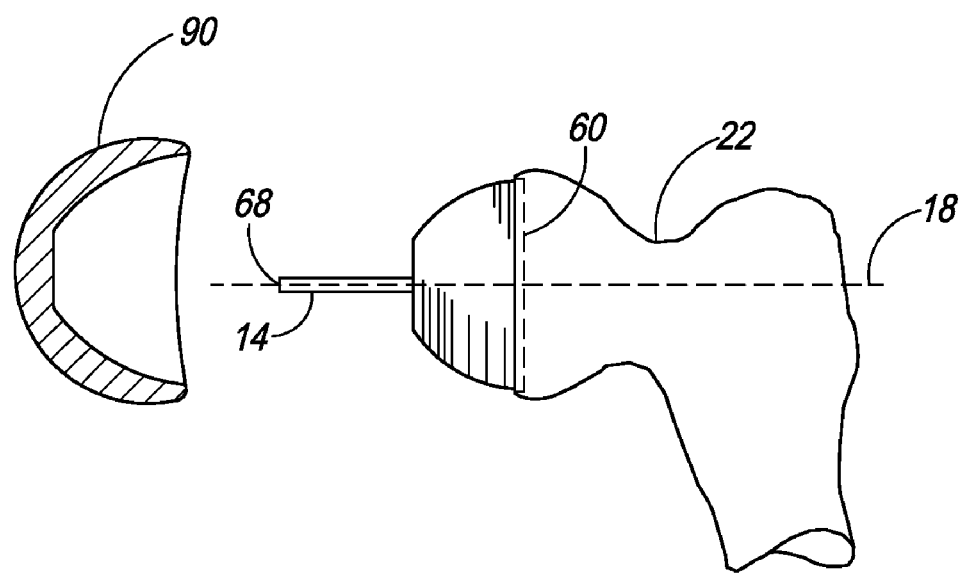

As shown in FIGS. 5A and 5B, the guide pin 14 can optionally be provided with a stop-shoulder 66. The stop-shoulder 66 acts to prevent the reamer 10 from cutting too deeply into the joint 20. This is accomplished by the end cutter 54 portion of the long planing teeth 50b coming against the stop-shoulder 66 and being prevented from sliding further down the guide pin 14. The shoulder 66 of the guide pin 14 is set to the desired maximum depth of the cut upon its installation in the joint 20.

Figure 6:
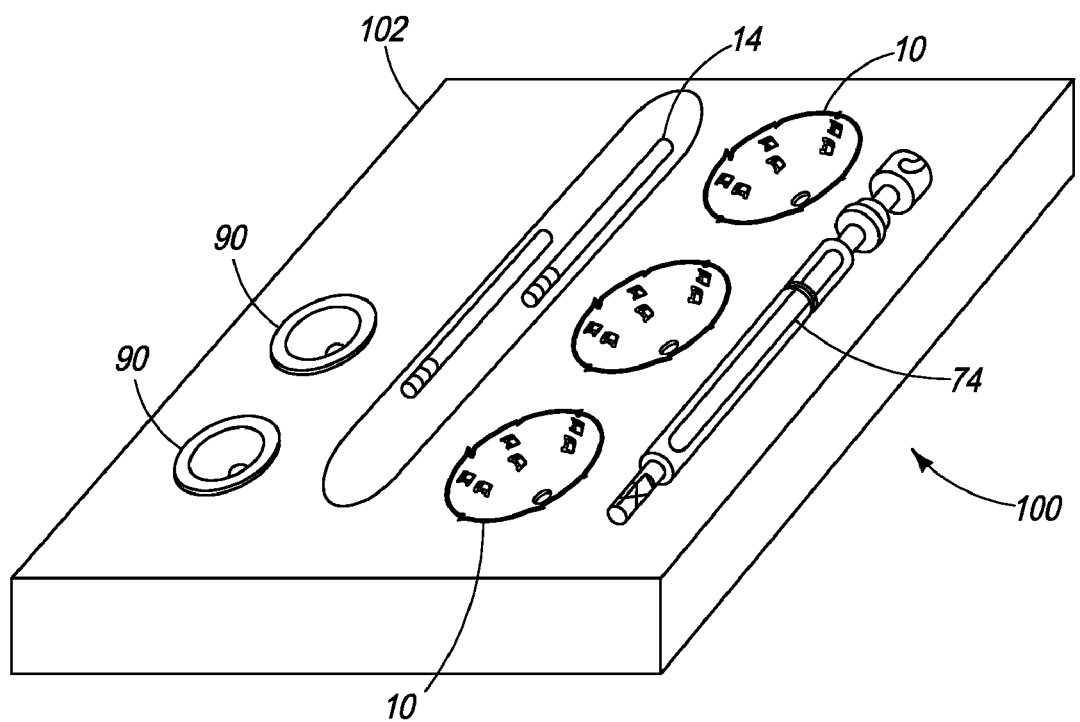
FIG. 6 is a perspective view of a tool kit of the invention.

Referring now to FIG. 6, a tool kit 100 is provided for cutting a defined profile suitable for mounting a prosthesis 90. The kit 100 includes at least one reamer 10, a reamer holder 74 capable of imparting torque to the at least one reamer; at least one guide pin 14 adapted to be received in a cannulation 12, 12a of the reamer, optionally, at least one prosthesis 90; and a case 102 for organizing components of the kit.

It should be noted that the invention may be implemented on a cylindrical reamer, a concave reamer, a conical reamer or a combination reamer.

In an advantage, the invention accurately cuts and efficiently shapes the bulbus bone joint in preparation for close fitting reception of a prosthetic cap.

In another advantage, the system of the invention guides a cutter so as to cut and shape the bulbus bone joint while not damaging it in the process.

In another advantage, the system of the invention enables controlled cutting and reshaping of the bulbus bone joint in preparation for the reception of a bone cap prosthesis.

In another advantage, the system of the invention allows for concurrent cutting of different surfaces of a bulbus bone joint, thus using fewer instruments (resulting in less overhead and less weight in tray), saving time, minimizing blood loss, lowering anaesthetic risk, and increasing surgical throughput.

In another advantage, the system uses highly efficient cutting teeth which generate less heat and therefore less cutting forces which otherwise might combine to overstress the stem of the bone joint, weakening it or causing it to fracture.

In another advantage, the invention is a combination inverted reamer having the advantage of being a single part with fewer operative steps, thereby reducing surgical time and increasing accuracy. The combination is enabled because of a superior design of cutting teeth that has a lower cutting torque and thus allows a cut on multiple simultaneous surfaces.

Multiple variations and modifications are possible in the embodiments of the invention described here. Although certain illustrative embodiments of the invention have been shown and described here, a wide range of modifications, changes, and substitutions is contemplated in the foregoing disclosure. In some instances, some features of the present invention may be employed without a corresponding use of the other features. Accordingly, it is appropriate that the foregoing description be construed broadly and understood as being given by way of illustration and example only, the spirit and scope of the invention.

What is claimed is:

1. A reamer, which comprises:
   a) a cutting form comprising a wall extending distally and outwardly along a longitudinal axis from a proximal cutting form portion having a first diameter to a distal rim having a second, greater diameter at a rim circumference;
   b) an axial guide having a guide length extending from a proximal guide end to a distal guide end, wherein the proximal cutting form portion is connected to the distal guide end;
   c) at least two radial bars, each having a proximal radial bar end attached to the axial guide and distal radial bar end that is not connected to either the axial guide or the cutting form; and
   d) wherein the rim is provided with a plurality of rim cutting teeth, each of them comprising a cutting face spaced from an immediately adjacent section of the rim in a forward, cutting direction by a relief space and wherein the rim cutting teeth alternate in pitch such that when viewed in the forward, cutting direction, a first one of the rim cutting teeth cuts beyond the outside surface of the cutting form with the next one cutting beyond the inside surface of the cutting form.

2. The reamer of claim 1 wherein the cutting face of each rim cutting tooth is oriented such that at least a portion of the face extends either outwardly or inwardly, as the case may be, from an imaginary outer or inner periphery of the rim circumference defined by a continuum of respective outer and inner radii extending from the longitudinal axis to the rim circumference of the cutting form.

3. The reamer of claim 1 wherein in addition to the cutting face of each rim cutting tooth being oriented either in an outwardly or an inwardly direction, each cutting face slopes in a distal direction extending past an imaginary plane defined by the immediately adjacent sections of the rim. forward of each rim cutting tooth.

4. The reamer of claim 1 wherein a plurality of planing teeth are radially disposed on an internal surface of the cutting form adjacent to the distal guide end.

5. The reamer of claim 4 wherein at least some of the radial planing teeth comprise an end cutter that extends to a position adjacent to an imaginary extension of an axial cannulation in the axial guide and wherein the cannulation is co-axial with the longitudinal axis of the cutting form.

6. The reamer of claim 1 wherein the axial guide comprises a central cannulation that passes from the proximal guide end to and through the distal guide end connected to the proximal cutting form portion.

7. The reamer of claim 1 wherein there are four radial bars extending outwardly from the axial guide.

8. The reamer of claim 7 wherein the four radial bars are disposed at 90° with respect to each other.

9. The reamer of claim 1 wherein the at least two radial bars extend in a plane at an intermediate location between the proximal guide end and the distal guide end.

10. The reamer of claim 1 wherein the cutting form. includes a plurality of wall cutting teeth formed in the wall thereof.

11. The reamer of claim 1 wherein the axial guide is provided with a clearance hole serving as a central cannulation for the reamer.

12. The reamer of claim 11 wherein the central cannulation in the axial guide is sized and surface treated to be a precise, sliding fit with a drill pin.

13. The reamer of claim 1 wherein the distal guide end includes a contact surface in a plane parallel to a plane of the at least two radial bars, wherein the contact surface prevents the cutting form from plunging so far over a bone as to potentially damage the bone stem.

14. The reamer of claim 13 wherein the contact surface is polished to reduce friction during relative rotational movement against a bone.

15. A tool kit for cutting a defined profile suitable for mounting a prosthesis, the kit including:
   a) at least one reamer according to claim 1;
   b) a reamer holder capable of imparting torque to the at least one reamer;
   c) at least one guide pin adapted to be received in a central cannulation that passes from the proximal guide end to and through the distal guide end connected to the proximal cutting form portion of the reamer;
   d) at least one prosthesis; and
   e) a case for organizing components of the kit.

16. A reamer, which comprises:
   a) a cutting form comprising a wall extending distally and outwardly along a longitudinal axis from a proximal cutting form portion having a first diameter to a distal rim having a second, greater diameter at a rim circumference;
   b) an axial guide having a guide length extending from a proximal guide end to a distal guide end, wherein the proximal cutting form portion is connected to the distal guide end;
   c) four radial bars, each having a proximal radial bar end attached to the axial guide and a distal radial bar end that is not connected to either the axial guide or the cutting form; and
   d) wherein the rim is provided with a plurality of rim cutting teeth, each of them comprising a cutting face spaced from an immediately adjacent section of the rim in a forward, cutting direction by a relief space and wherein the rim cutting teeth alternate in pitch such that when viewed in a cutting direction, a first one of the rim cutting teeth cuts beyond the outside surface of the cutting form with the next one cutting beyond the inside surface of the cutting form.

17. The reamer of claim 16 wherein the cutting face of each rim cutting tooth. is oriented such that at least a portion of the face extends either outwardly or inwardly, as the case may be, from an imaginary outer or inner periphery of the rim circumference defined by a continuum of respective outer and inner radii extending from the longitudinal axis to the rim circumference of the cutting form.

18. The reamer of claim 16 wherein in addition to the cutting face of each rim cutting tooth being oriented either in an outwardly or an inwardly direction, each cutting face slopes in a distal direction extending past an imaginary plane defined by the immediately adjacent sections of the rim forward of each rim cutting tooth.

19. The reamer of claim 16 wherein the radial bars are disposed at 90° with respect to each other extending outwardly from the axial guide.

20. The reamer of claim 16 wherein the radial bars extend in a plane at an intermediate location between the proximal guide end and the distal guide end.

21. The reamer of claim 16 wherein the cutting form includes a plurality of wall cutting teeth.

22. A reamer system, which comprises:
   a) a reamer, comprising:
      i) a cutting form comprising a wall extending distally and outwardly along a longitudinal axis from a proximal cutting form portion having a first diameter to a distal rim having a second, greater diameter at a rim circumference;
      ii) an axial guide having a. guide length extending from a proximal guide end to a distal guide end, wherein the proximal cutting form portion is connected to the distal guide end;
      iii) at least two radial bars, each having a proximal radial bar end attached to the axial guide and a distal radial bar end that is not connected to either the axial guide or the cutting form;
      iv) wherein the rim is provided with a plurality of rim cutting teeth, each of them comprising a cutting face spaced from an immediately adjacent section of the rim in a forward, cutting direction by a relief space and wherein the rim cutting teeth alternate in pitch such that when viewed in a cutting direction, a first one of the rim cutting teeth cuts beyond the outside surface of the cutting form with the next one cutting beyond the inside surface of the cutting form; and
      vi) a central cannulation that passes from the proximal guide end to and through the distal guide end connected to the proximal cutting form portion; and
   b) a reamer holder having a bayonet locking mechanism capable of locking the holder to the reamer at the radial bars.

23. The reamer system of claim 22 wherein the cutting face of each rim cutting tooth is oriented such that at least a portion of the face extends either outwardly or inwardly, as the case may be, from an imaginary outer or inner periphery of the rim circumference defined by a continuum of respective outer and inner radii extending from the longitudinal axis to the rim circumference of the cutting form.

24. The reamer system of claim 22 wherein in addition to the cutting face of each rim cutting tooth being oriented either in an outwardly or an inwardly direction, each cutting face slopes in a distal direction extending past an imaginary plane defined by the immediately adjacent sections of the rim forward of each rim cutting tooth.

25. The reamer system of claim 22 wherein the bayonet locking mechanism includes recesses which catch portions of the bars.

26. The reamer system of claim 22 wherein the reamer holder has a central cannulation permitting a drill pin to pass therethrough.

27. The reamer system of claim 26 wherein the cannulation in the axial guide is sized and surface treated to be in a precise, sliding fit with a drill pin.

28. The reamer system of claim 22 wherein the cutting form of the reamer includes a plurality of wall cutting teeth.

* * * * *